United States Patent [19]

Payne

[11] 4,306,127
[45] Dec. 15, 1981

[54] CORROSION SENSOR

[75] Inventor: Frank Payne, Knoxville, Tenn.

[73] Assignee: Robertshaw Controls Company, Richmond, Va.

[21] Appl. No.: 132,340

[22] Filed: Mar. 20, 1980

[51] Int. Cl.³ ............................................ H01H 35/38
[52] U.S. Cl. ............................. 200/61.04; 200/83 J; 137/67
[58] Field of Search ............... 200/61.04, 61.05, 82 C, 200/86 A, 83 J, 83 N, 83 B, 61.06, 61.08; 137/67

[56] References Cited
U.S. PATENT DOCUMENTS

| 2,744,977 | 5/1956 | Lombard et al. | 200/83 J |
| 3,553,967 | 1/1971 | Porter | 200/86 A |
| 3,630,216 | 12/1971 | Kelly | 137/67 |
| 3,787,650 | 1/1974 | Lewis | 200/61.04 |

Primary Examiner—J. D. Miller
Assistant Examiner—D. L. Rebsch
Attorney, Agent, or Firm—Candor, Candor & Tassone

[57] ABSTRACT

A corrosion sensor having a housing carrying an electrical switch that has an actuator normally held in one switch operating position thereof by a corrosion sensing member of the housing and moving to another switch operation position thereof when the corrosion sensing member ruptures through the corrosion thereof caused by being exposed to a corrosive area, the corrosion sensing member also comprising a seal member for normally sealing the switch structure from the corrosive area until the corrosion sensing member ruptures. The housing has a chamber therein containing the switch and has an end provided with an opening leading to the chamber. The corrosion sensing member spans the opening to seal the chamber from the corrosive area. A flexible diaphragm is carried by the housing in stacked engaging relation with the corrosion sensing member and also spans the opening immediately adjacent the corrosion sensing member and intermediate the corrosion sensing member and the switch to seal the chamber from the corrosive area when the corrosion sensing member ruptures.

12 Claims, 4 Drawing Figures

CORROSION SENSOR

BACKGROUND OF THE INVENTION

1. Field of the Invention

This invention relates to a corrosion sensor.

2. Prior Art Statement

It is known to applicant to provide a corrosion sensor having a housing means carrying an electrical switch means that has an actuator means normally held in one switch operating position thereof by a corrosion sensing member of the housing means and moving to another switch operating position thereof when the corrosion sensing member ruptures through the corrosion thereof caused by being exposed to a corrosive area so that the switch means will operate indicating means to indicate that the corrosive action taking place in the corrosive area is at an adverse level, the corrosive area being any desired fluid area, such as a heat exchanger fluid flow path means for a solar energy collecting system or the like.

Such prior known corrosion sensor has the corrosion sensing member thereof comprising an aluminum wire that holds a spring biased actuator of the switch means in its one operating position until the aluminum wire is sufficiently eaten away by the corrosive action of the corrosive area to permit the spring loaded actuator to break the strip of aluminum wire and move the switch means to its other operating position and thereby cause an indicator to indicate that such a corrosive action has taken place. The spring biased actuator includes a plunger that is covered by a resilient sealing boot that extends from the switch housing to the free end of the plunger.

The U.S. Patent to Lewis, U.S. Pat. No. 3,787,650, discloses a warning mechanism to indicate the presence of an impurity in a tube carrying a fluid and has a resin film-like member closing an open end of the housing that contains an electrical switch, the film-like member holding a plunger of the switch in one operating position thereof and sealing the chamber from the switch. When the film-like member ruptures, the same permits the spring biased plunger to move through the ruptured film-like member to actuate the switch to its indicating condition thereof.

SUMMARY OF THE INVENTION

It is a feature of this invention to provide an improved corrosion sensor wherein the corrosion sensing member thereof performs a dual function, namely, acts as a corrosion sensing member and also acts as a seal member that protects the remainder of the structure of the corrosion sensor from the corrosive action present at the corrosive area being monitored thereby.

In particular, it is known to applicant to provide a corrosion sensor having a housing means carrying an electrical switch means that has an actuator means normally held in one switch operating position thereof by a corrosion sensing member of the housing means and moving to another switch operating position thereof when the corrosion sensing member ruptures through the subsequent corrosion thereof caused by being exposed to a corrosive area.

However, it was found according to the teachings of this invention, that since the corrosion sensing member of such prior known corrosion sensor comprised a length of an aluminum wire that spans an opening of the corrosion sensor in a manner to hold a spring biased plunger actuator of the switch means in its one operating position until the wire ruptures sufficiently to permit the springloaded actuator to move the switch construction to its other signal-producing operating condition, various parts of the prior known corrosion sensor are subject to the corrosive action existing in the corrosive area being monitored thereby.

Thus, it was found according to the teachings of this invention, that the corrosion sensing member could perform such previously described corrosion sensing function and also provide a seal member for normally sealing the switch means of the corrosion sensor from the corrosive area at least until the corrosion sensing member ruptures.

Accordingly, one embodiment of this invention provides a corrosion sensor having a housing means carrying an electrical switch means that has an actuator means normally held in one switch operating position thereof by a corrosion sensing member of the housing means and moving to another switch operating position thereof when the corrosion sensing member ruptures through the corrosion therof caused by being exposed to a corrosive area, the corrosion sensing member also comprising a seal member for normally sealing the switch means from the corrosive area until the corrosion sensing member ruptures. The housing means has a chamber therein containing the switch means and has an end provided with an opening leading to the chamber. The corrosion sensing member spans the opening to seal the chamber from the corrosive area. A flexible diaphragm is carried by the housing means in stacked engaging relation with the corrosion sensing member and also spans the opening immediately adjacent the corrosion sensing member and intermediate the corrosion sensing member and the switch means to seal the chamber from the corrosive area when the corrosion sensing member ruptures.

Accordingly, it is an object of this invention to provide an improved corrosion sensor having one or more of the novel features of this invention as set forth above or herinafter shown or described.

Another object of this invention is to provide a method of making such a corrosion sensor, the method of this invention having one or more of the novel features of this invention as set forth above or hereinafter shown or described.

Other objects, uses and advantages of this invention are apparent from a reading of this description which proceeds with reference to the accompanying drawings forming a part thereof and wherein:

DESCRIPTION OF THE PREFERRED EMBODIMENT

Figure 1:
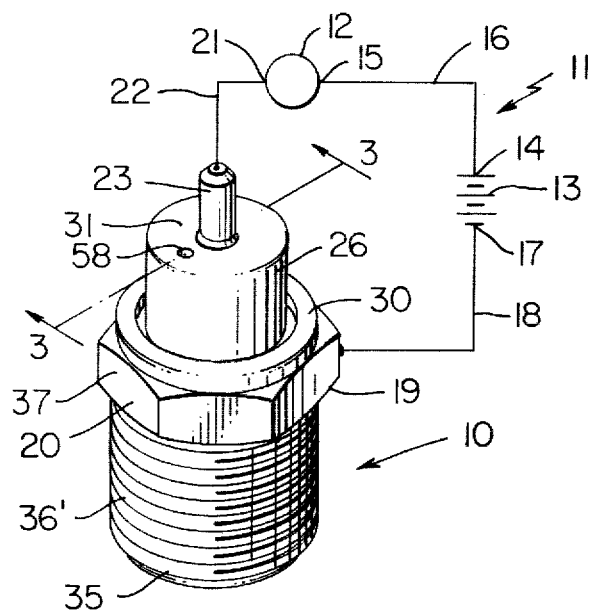
FIG. 1 is a perspective view of the improved corrosion sensor of this invention, FIG. 1 also schematically illustrating a corrosion sensing system utilizing the corrosion sensor of this invention.

While the various features of this invention are hereinafter described and illustrated as being particularly adapted to provide a corrosion sensor for monitoring the corrosive action in the fluid of a heat exchanger system, it is to be understood that the various features of this invention can be utilized singly or any combination thereof to provide a corrosion sensor for other types of apparatus as desired.

Therefore, this invention is not to be limited to only the embodiment illustrated in the drawings, because the drawings are merely utilized to illustrate one of the wide variety of uses of this invention.

Referring now to FIG. 1, the improved corrosion sensor of this invention is generally indicated by the reference numeral 10 and is illustrated as being utilized in a corrosion sensor system that is generally indicated by the reference numeral 11 and comprising an electrically operated indicator 12 and an electrical power source 13 having one side 14 thereof interconnected to one side 15 of the indicating device 12 by a lead means 16 and the other side 17 thereof interconnected by a lead means 18 to an electrically conductive housing member 19 of the housing means 20 of the temperature sensor 10.

Figure 3:
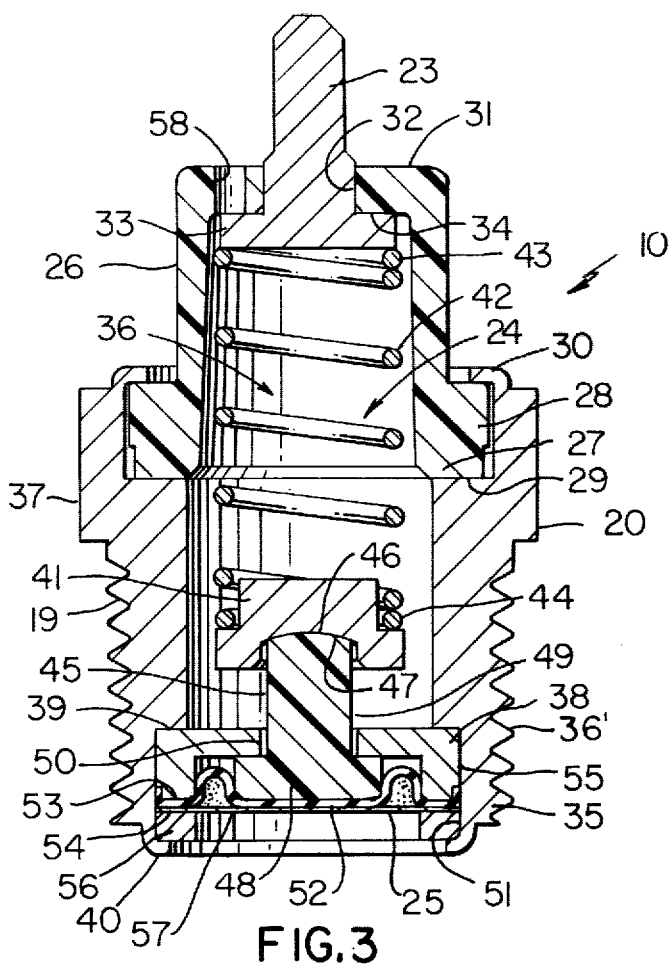
FIG. 3 is an enlarged cross-sectional view taken on lines 3—3 of FIG. 1 and illustrates the corrosion sensor in one operating position thereof.
Figure 4:
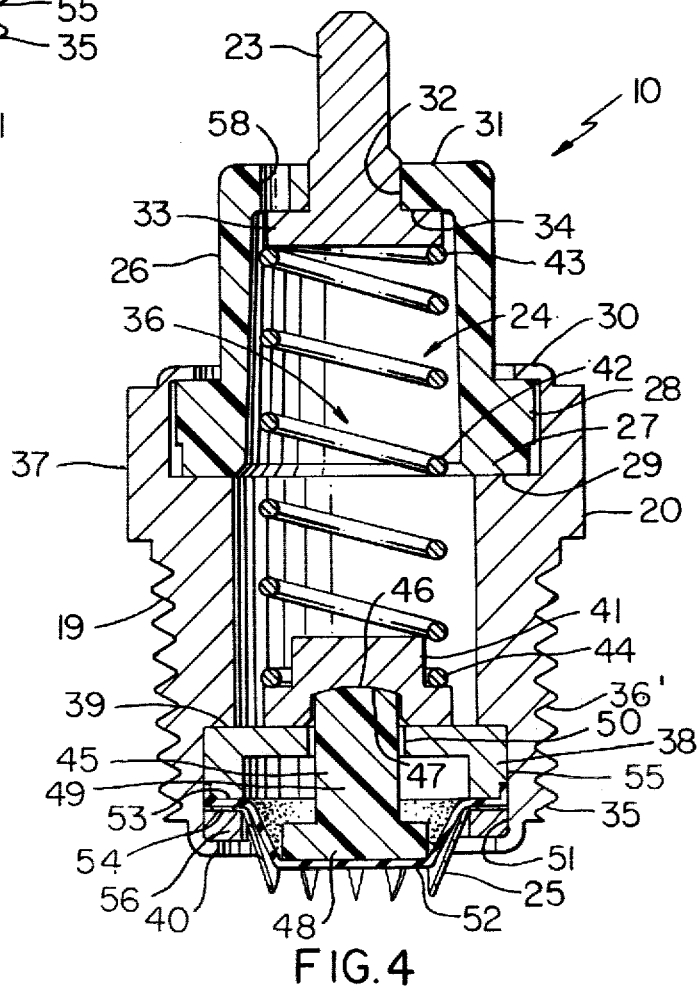
FIG. 4 is a view similar to FIG. 3 and illustrates the corrosion sensor after the same has been actuated to an adverse corrosion indicating condition thereof.

The other side 21 of the indicator 12 is interconnected by a lead 22 to a contact means 23 of the corrosion sensor 10 so that when an electrical switch means, generally indicated by the reference numeral 24 in FIGS. 3 and 4, is in the actuated position illustrated in FIG. 4, an electrical circuit is completed through the indicating device 12 so that the same is electrically operated by the source 13 to indicate that a corrosion sensing member 25 of the corrosion sensor 10 has been ruptured sufficiently by a corrosive action as illustrated in FIG. 4 to cause the switch means 24 to be in the actuated condition of FIG. 4.

However, when the corrosion sensing member 25 is in its non-ruptured condition of FIG. 3, the switch means 24 is held in an open position as will be apparent hereinafter so that the electrical circuit from the source 13 through the indicator 12 cannot be completed whereby the indicator 12 will indicate that an adverse corrosive action has not taken place.

The housing means 20 of the temperature sensor 10 of this invention comprises another housing member 26 secured to the housing member 19 in aligned relation therewith and is formed from a suitable electrically insulating material, the housing member 26 being substantially cup-shaped and having its open end 27 provided with outwardly directed annular flange 28 which abuts against an annular shoulder 29 of the housing member 19 to be held thereto by a subsequently turned-over or staked end 30 of the housing member 19 as illustrated in FIGS. 3 and 4 whereby the housing members 19 and 26 are secured together by the turning or staking operation of the end 30 of the housing member 19 to the flange 28 of the housing member 26.

The housing member 26 has a closed end 31 provided with a central opening 32 passing therethrough and through which the electrical contact means 23 projects, the contact means 23 having an enlarged head 33 which abuts against the inside surface 34 of the closed end 31 of the housing member 26 to prevent the same from passing completely through the housing member 26.

The housing member 19 is substantially tubular and defines a lower open end 35 as illustrated in FIG. 3 which is subsequently closed in a manner hereinafter described, the housing members 19 and 26 operating together to define a chamber 36 for containing the switch means 24 therein.

The housing member 19 is provided with a externally threaded portion 36' for threading the corrosion sensor 10 into a suitable threaded opening of a conduit system or the like so as to expose the lower end 35 of the corrosion sensor 10 to the corrosive action of the fluid or liquid passing through such conduit system, such as the heat exchanger fluid in a solar energy collector system or the like.

The housing member 19 is also provided with a hex-shaped section 37 to facilitate such threading of the threaded section 36' of the corrosion sensor 10 in a manner well known in the art.

The electrical switch means 24 for the corrosion sensor 10 includes the contact means 23 previously described and another contact means 38 held against an anuular shoulder 39 of the housing member 19 by a turned-over portion 40 of the end 35 of the housing member 19 in a manner hereinafter described whereby the electrical contact means 38 is disposed in electrical connection with the housing member 19. Thus, by having the lead 18 of the system 11 interconnected to the housing member 19, such lead is, in effect, electrically interconnected to the contact means 38.

Of course, it is to be understood that the housing member 19 could be effectively interconnected to a ground potential by the conduit system being monitored thereby so that a hot lead is interconnected to the contact means 23 to permit electrical current to flow through the indicator 12 only when the lead 22 thereof is interconnected to ground as would be the case when the contact means 23 is interconnected to the contact means 38 in a manner hereinafter described.

An electrically conductive and movable switching member 41 is disposed in the chamber 36 of the housing means 20 and is electrically interconnected to the contact means 23 by a conductive compression spring 42 having one end 43 thereof bearing against the enlarged end 33 of the contact means 23 to hold the same against the end wall surface 34 and having its other end 44 bearing against the switching member 41 which forms a spring seat therefor whereby the force of the compression spring 42 tends to urge the switching member 41 into electrical contact with the contact means 38 to complete an electrical circuit between the contact means 23 and 38 for a purpose hereinafter described.

The electrical switch means 24 of the corrosion sensor 10 includes an actuator member 45 formed of any suitable electrically insulating material and having one end 46 thereof projecting into a recess 47 of the conductive spring seat 41 and bear thereagainst so as to move in unison therewith, the other end 48 of the actuator 45 being disc-like whereby a body portion 49 of the actuator 45 is adapted to project through a central opening 50 formed through the contact means 38 to hold the switching member 41 out of electrical contact with the contact means 38 when the end 48 of the actuator 45 is bearing against the contact means 38 as illustrated in FIG. 3 and being held thereagainst by the corrosion sensing member 25 that spans and seals the opening 51 disposed at the end 35 of the temperature sensor 10 in a manner hereinafter set forth.

A flexible diaphragm 52 is interposed between the actuator 45 and the corrosion sensing member 25 and has its outer peripheral portion 53 disposed in stacked relation with the outer peripheral portion 54 of the corrosion sensing member 25 between the outer annular flange portion 55 of the contact means 38 and an annular retainer ring 56 that is held in stacked relation against the exposed side 57 of the corrosion sensing member 25 by the subsequently turned-over or stacked portion 40 of the housing member 19 as illustrated in FIG. 3.

Figure 2:
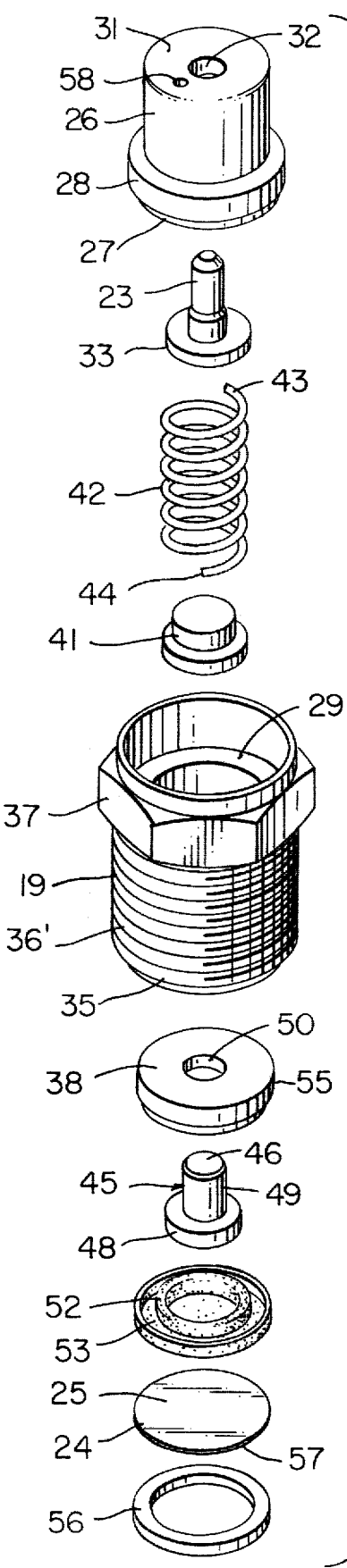
FIG. 2 is an exploded perspective view of the various parts of the corrosion sensor of FIG. 1.

The corrosion sensing member 25 is formed from aluminum foil and is in disc-like form illustrated in FIG. 2 so that the same completely spans and seals closed the opening 51 at the end 35 of the housing member 29 so as to completely protect and seal the remainder of the electrical switch means 24 from the corrosive area that will be exposed to the side 57 of the corrosion sensing member 25 when the housing means 20 is threaded into a threaded opening of the conduit system containing such corrosive area.

The flexible diaphragm 52 also seals the switch means 24 from the corrosive area once the corrosive sensing member 25 ruptures in a manner illustrated in FIG. 4 as will be apparent hereinafter.

Therefore, it can be seen that the electrical switch means 24 of the sensor 10 of this invention comprises the contact means 23 and 38, the conductive compression spring 42, the spring seat 41 and the actuator 45 that is normally held in the non-switching condition of FIG. 3 by the corrosion sensing member 25 remaining in its disc-like form and causing elecrical connection between the contact means 23 and 38 through the conductive spring 42 and conductive spring seat 41 only when the corrosion sensing member 25 ruptures in the manner illustrated in FIG. 4 through the corrosive material eating into the corrosion sensing member 25 sufficiently to cause the same to rupture under the force of the compression spring 42.

During the assemblying of the corrosion sensor 10 of this invention from the parts illustrated in FIG. 2, it is preferred that the contact means 38, actuator 45, flexible diaphragm 52, corrosion sensing member 25 and retaining means 56 first be assembled to the housing member 19 through the turning over of the end portion 40 of the housing member 19 before the housing member 19 is secured to the housing member 26 through the turning over of the portion 30 of the housing member 19 so that the corrosion sensing member 25 is held straight across the opening 51 of the housing member 19 and is held in such initial flat manner by the turned-over portion 40 of the housing member 19 before any of the spring force is imposed thereon by the spring 42 which occurs during the subsequent assemblying of the spring 42, the seat 41, the contact 23 and the housing member 26 being secured to the housing member 19 by the turning over of the portion 30 of the housing member 19.

Thus, it can be seen that when the corrosion sensor 10 of this invention is initially formed, the same is in the condition illustrated in FIG. 3 where the switching member 41 is held out of electrical contact with the contact means 38 by the electrically insulating actuator 45 that is held in the position as illustrated in FIG. 3 by the corrosion sensing member 25.

In order to prevent a dash-pot effect of the chamber 36, a vent opening 58 is formed through the closed end 31 of the housing member 26 in an offset relation to the enlarged end 33 of the contact means 23.

Therefore, it can be seen that it is a relatively simple method of this invention to form the temperature sensor 10 of this invention from the improved parts thereof to operate in a manner now to be described.

After the corrosion sensor 10 of this invention has been inserted into a threaded opening of a conduit system containing a fluid to have the corrosive action thereof monitored, the projecting contact 23 thereof is interconnected by the lead 22 to the indicator 12 and the side 17 of the source 13 is, in effect, interconnected to the housing member 19 by the lead means 18 whereby the indicator 12 remains in its nonactivated condition as long as the corrosion sensing member 25 remains in the stable disc-like condition illustrated in FIG. 3 that holds the switching member 41 out of electrical contact with the contact means 38 in opposition to the force of the compression spring 42 as illustrated in FIG. 3. During this time, the corrosion sensing member 25 completely spans and seals the opening 51 at the end 35 of the housing member 19 so that the corrosive fluid that is exposed to the side 57 of the corrosion sensing member 25 cannot reach the flexible diaphragm 52 and attack the same whereby the corrosion sensing member 25 of this invention performs the dual function of sensing the corrosive action of the corrosive area being monitored and providing a seal for the switch means 24 of the sensor 10.

However, when the corrosive action of the corrosive fluid being exposed to the side 57 of the corrosion sensing member 25 has eaten away a sufficient amount of the corrosion sensing member 25 so as to reduce its strength in opposing the force of the compression spring 42, the force of the compression spring 42 causes the actuator 45 and diaphragm 52 to rupture through the corrosion sensing member 25 in the manner illustrated in FIG. 4 and thereby permit the conductive spring seat 41 to make contact with the contact means 38 and thereby complete the electrical circuit between contact means 30 and 38. In this manner, the indicator 12 indicates that the corrosion sensor 10 has been activated by an adverse corrosion effect in the system being monitored thereby and that the system being monitored by the sensor 10 needs attention to correct the corrosive condition thereof.

Once the corrosive action in the system has been corrected, the corrosion sensor 10 of FIG. 4 can be replaced by a new corrosion sensor 10 which is in the condition of FIG. 3 so as to again monitor the system utilizing the same.

Thus, it can be seen that this invention not only provides an improved corrosion sensor, but also this invention, provides an improved method of making such a corrosion sensor.

While the form and method of this invention now preferred have been illustrated and described as required by the Patent Statute, it is to be understood that other forms and method steps can be utilized and still fall within the scope of the appended claims.

What is claimed is:

1. In a corrosion sensor having a housing means carrying an electrical switch means that has an actuator means normally held in one switch operating position thereof by a corrosion sensing member of said housing means and moving to another switch operating position thereof when said corrosion sensing member ruptures through the corrosion thereof caused by being exposed to a corrosive area, said corrosion sensing member also comprising a seal member for normally sealing said switch means from said corrosive area until said corrosion sensing member ruptures, said housing means having a chamber therein containing said switch means, said housing means having an end provided with an opening leading to said chamber, said corrosion sensing member spanning said opening to seal said chamber from said corrosive area, the improvement comprising a flexible diaphragm carried by said housing means in stacked engaging relation with said corrosion sensing member and also spanning said opening immediately adjacent said corrosion sensing member and intermediate said corrosion sensing member and said switch means to seal said chamber from said corrosive area when said corrosion sensing member ruptures.

2. A corrosion sensor as set forth in claim 1 wherein said corrosion sensing member comprises a sheetlike metallic foil member.

3. A corrosion sensor as set forth in claim 2 wherein said corrosion sensing member comprises aluminum foil.

4. A corrosion sensor as set forth in claim 1 wherein said switch means includes first and second contact means and a movable switching means for interconnecting said contact means together when said actuator means is in said other switch operating position thereof.

5. A corrosion sensor as set forth in claim 4 wherein said actuator means includes a movable electrically insulating member disposed between and against said switching means and said diaphragm.

6. A corrosion sensor as set forth in claim 5 wherein said switching means includes an electrically conductive compression spring having opposed ends and an electrically conductive spring seat, said spring having one of said ends thereof disposed in electrical contact with said first contact means and having the other of said ends thereof bearing in electrical contact with said seat, said electrically insulating member being disposed against said seat, said second contact means being disposed intermediate said seat and said diaphragm.

7. A corrosion sensor as set forth in claim 6 wherein said first contact means, said spring, said seat, said electrically insulating member, said diaphragm and said corrosion sensing member are disposed in axially aligned relation in said housing means.

8. A corrosion sensor as set forth in claim 7 wherein said housing means includes first and second housing members secured together in aligned relation, said first housing member being formed of electrically insulating material and electrically spacing said first contact means from said second contact means.

9. A corrosion sensor as set forth in claim 8 wherein said second housing member is formed of electrically conducting material and carries said second contact means, said diaphragm and said corrosion sensing member in aligned relation.

10. A corrosion sensor as set forth in claim 9 wherein an annular retainer ring is held by said second housing member against said corrosion sensing member on the side thereof opposite to said flexible diaphragm.

11. A corrosion sensor as set forth in claim 10 wherein said second housing member has an annular shoulder and a turned end spaced from said shoulder, said second contact means being disposed against said shoulder, said diaphragm and said corrosion sensing member and said retainer member being disposed against said second contact means in serial stacked relation, said turned end of said second housing member being turned against said retainer member.

12. A corrosion sensor as set forth in claim 11 wherein said second contact means has a opening therethrough, said electrically insulating member projecting through said opening of said second contact means.

* * * * *